United States Patent [19]
Ornstein

[11] Patent Number: 5,446,051
[45] Date of Patent: Aug. 29, 1995

[54] ARYL-SPACED DECAHYDROISOQUINOLINE-3-CARBOXYLIC ACIDS AS EXCITATORY AMINO ACID RECEPTOR ANTAGONISTS

[75] Inventor: Paul L. Ornstein, Carmel, Ind.

[73] Assignee: Eli Lilly and Company, Indianapolis, Ind.

[21] Appl. No.: 251,809

[22] Filed: May 31, 1994

[51] Int. Cl.$^6$ .................... C07D 217/06; A61K 31/47
[52] U.S. Cl. ...................... 514/307; 546/22; 546/147
[58] Field of Search .......... 546/22, 146, 147; 514/307

[56] References Cited

U.S. PATENT DOCUMENTS

| | | | |
|---|---|---|---|
| 4,902,695 | 2/1990 | Ornstein | 514/307 |
| 5,284,957 | 2/1994 | Huff | 548/112 |

Primary Examiner—C. Warren Ivy
Assistant Examiner—Zinna N. Davis
Attorney, Agent, or Firm—Martin A. Hay; Thomas J. Dodd; David E. Boone

[57] ABSTRACT

The present invention provides novel decahydroisoquinoline derivatives which are useful as excitatory amino acid antagonists. The invention also provides for methods of using these derivatives to treat various neurological disorders.

40 Claims, No Drawings

ARYL-SPACED DECAHYDROISOQUINOLINE-3-CARBOXYLIC ACIDS AS EXCITATORY AMINO ACID RECEPTOR ANTAGONISTS

FIELD OF THE INVENTION

This invention relates to excitatory amino acid receptor antagonists, and will have particular application to antagonists which are AMPA site selective.

Background of the Invention

In the mammalian central nervous system (CNS), the transmission of nerve impulses is controlled by the interaction between a neurotransmitter and a surface receptor. Neurotransmitters, such as L-glutamate and L-aspartate, are released by sending neurons and travel across the synapse where they interact with the surface receptor of the receiving neuron. Such neurotransmitters are referred to as excitatory amino acids (EAA's) because they mediate the major excitatory pathways in the CNS. Likewise, the surface receptors of the receiving neurons are generally referred to as EAA receptors.

EAA receptors are of two principal classes; the "ionotropic" receptors, which are directly coupled to cation channels in the cell membrane; and the "metabotropic" receptors which are coupled through G-proteins to multiple second messenger systems that produce either enhanced phosphoinositide (PI) hydrolysis, or activation of phospholipase D, or changes in cAMP formation or changes in ion channel function.

There are three major subclasses of ionotropic receptors, based upon their sensitivity to a selective agonist. The three subclasses are generally referred, to as the N-methyl-D-aspartate (NMDA) group; the α-amino-3-hydroxy-5-methyl-isoxazole-4 propionic acid (AMPA) group; and the kainic acid (KA) group.

EAA's and their receptors play an important role in a variety of physiological processes, such as long-term potentiation (LTP), synaptic plasticity, motor control, respiration, cardiovascular regulation and sensory perception.

Excessive or inappropriate stimulation of EAA receptors may lead to neuronal cell damage or cell death. This phenomenon is often referred to as excitotoxicity. Excitotoxicity has been suggested as the major cause of neuronal degeneration in a number of CNS diseases and conditions, such as Alzheimer's Disease, Huntington's Chorea, amyotrophic lateral sclerosis (ALS), cerebral ischemia and many other related neurodegenerative diseases.

It has been suggested that the blocking actions of antagonist compounds can abate the cell death caused by excitotoxicity. Selective antagonists which block the action of certain types or subtypes of EAA receptors have been synthesized and tested in the past, particularly at the NMDA receptors. A prior example of an AMPA selective antagonist is described and claimed in U.S. Pat. No. 5,284,957. Selective antagonists could be particularly useful in individuals who demonstrate receptor selective excitotoxicity.

SUMMARY OF THE INVENTION

The present invention provides novel compounds that affect EAA receptors, particularly the AMPA (α-amino-3-hydroxy-5-methylisoxazole-4-propionic acid) receptors. Preferably, the compounds are of the general formula

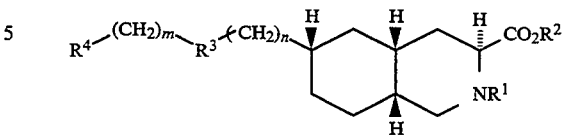

wherein $R^1$ is H, $C_1-C_{10}$ alkyl, arylalkyl, alkoxycarbonyl, aryloxycarbonyl, or acyl;

$R_2$ is H, $C_1-C_6$ alkyl, substituted alkyl, $C_4-C_7$ cycloalkyl or arylalkyl;

$R_3$ is aryl, arylalkyl, heterocycle, substituted heterocycle, $C_4-C_7$ cycloalkyl or $C_4-C_7$ cycloalkenyl;

$R^4$ is $CO_2H$, $SO_3H$, $PO_3H_2$, or one of the following cyclic compounds:

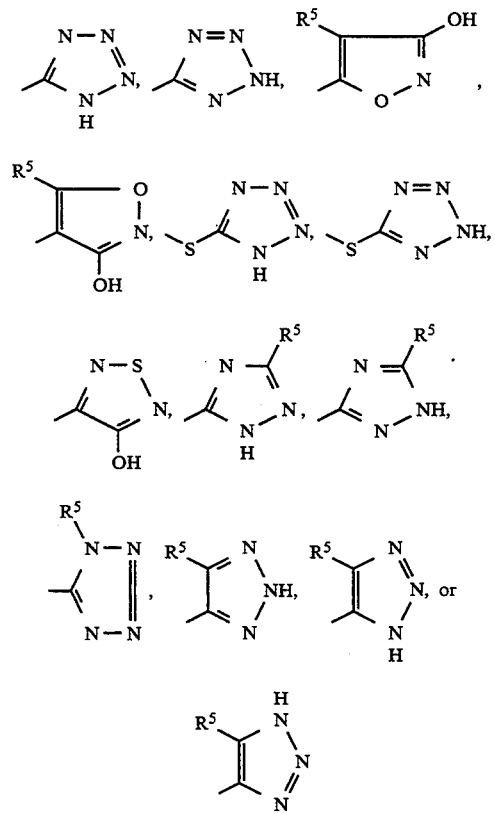

wherein
$R^5$ is H, $C_1-C_6$ alkyl or aryl;
m=0, 1 or 2; and
n=0, 1 or 2;
or a pharmaceutically acceptable salt thereof.

The invention further provides for the use of Formula (I) compounds, preferably as AMPA selective EAA antagonists. The invention also provides pharmaceutical formulations which incorporate compounds of Formula (I) and a pharmaceutically acceptable carrier, diluent or excipient thereof.

Use of Formula (I) compounds as AMPA selective antagonists is seen as potentially beneficial in treating a number of neurodegenerative conditions including, but not limited to Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, cognitive disorders, Parkinson's Disease, anxiety, emesis, brain edema, chronic pain and tardive dyskinesia, among others. Formula (I) compounds are also contemplated for use to abate cerebral deficits subsequent to cardiac bypass surgery and grafting, stroke, cerebral ischemia, and spinal cord and brain trauma injuries. Further, Formula (I) compounds are contemplated for use as analgesic agents.

DETAILED DESCRIPTION OF THE INVENTION

The term "$C_1$–$C_{16}$ alkyl" represents a straight or branched alkyl chain having from one to sixteen carbon atoms. Typical straight or branched $C_1$–$C_{16}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl and the like. The term "$C_1$–$C_{16}$ alkyl" includes within it the terms "$C_1$–$C_4$ alkyl", "$C_1$–$C_6$ alkyl", and $C_1$–$C_{10}$ alkyl".

The term "$C_4$–$C_7$ cycloalkyl" represents a cyclic alkyl group having four to seven carbon atoms. Typical $C_4$–$C_7$ cycloalkyl groups include cyclobutyl, cyclopentyl, cyclohexyl and cycloheptyl.

The term "acyl" represents a hydrogen or a $C_1$–$C_6$ alkyl group attached to a carbonyl group. Typical acyl groups include formyl, acetyl, propanoyl, butanoyl, pentanoyl, and hexanoyl.

The term "carboxy protecting group" as used herein refers to one of the ester derivatives of the carboxylic acid group, which then protects this group while reactions are carried out on other functional groups. Examples include methyl, ethyl, benzyl, 4-nitrobenzyl, 4-methoxybenzyl, 3,4-dimethoxybenzyl, 2,4-dimethoxybenzyl, 2,4,6-trimethoxybenzyl, 2,4,6 trimethylbenzyl, benzhydryl, t-butyl, t-amyl, trityl, trimethylsilyl, t-butyldimethylsilyl, 2-trimethylsilylethyl, and the like.

The term "nitrogen protecting group" as used herein refers to substituents on amino groups that are commonly employed to block or protect an amino functionality. Examples of nitrogen protecting groups include benzyl, formyl, trityl, trifluoroacetyl, trichloroacetyl, chloroacetyl, benzyloxycarbonyl, methoxycarbonyl, t-butoxycarbonyl 2-trimethylsilylethoxycarbonyl, 2,2,2-trichloroethoxycarbonyl, and the like.

The term "aryl" represents an aromatic radical, such as phenyl, and polynuclear aromatic radicals, such as naphthyl, fluorenyl, anthracyl and phenanthrenyl. The term "substituted aryl" represents an aryl group substituted with one or more moieties chosen from the group consisting of halogen, hydroxy, cyano, nitro, $C_1$–$C_6$ alkyl, $C_1$–$C_4$ alkoxy, carboxy, acetyl, formyl, carboxymethyl, hydroxymethyl, amino, aminomethyl or trifluoromethyl. Examples of substituted aryl groups include 4-methylphenyl, 2-methylphenyl, 4-methoxyphenyl, 4-(i-propyl)phenyl, 4-cyclopentylphenyl, 4-(t-butyl)phenyl, 4-acetylphenyl, 4-trifluoromethylphenyl, 4-chlorophenyl, 2-bromophenyl, 3-iodophenyl, 6-bromonaphthyl, 3,4-(methylenedioxy)phenyl, indanyl, 1,2,3,4-tetrahydronaphthyl, and 1,2,4,4-tetramethyl-1,2,3,4-tetrahydronaphthyl.

The term "arylalkyl" represents a $C_1$–$C_4$ alkyl group bearing an aryl group. Representatives of arylalkyl groups include benzyl, 1-phenylethyl, 2-phenylethyl, 3-phenylpropyl, 4-phenylbutyl, 2-methyl-2 phenylpropyl, ( 4-chlorophenyl)methyl, (2,6-dichlorophenyl)methyl, (4-hydroxyphenyl)methyl, (2,4-dinitrophenyl)methyl or the like. The term "heterocycle" represents a five-membered or six membered ring, which contains one to four heteroatoms selected from oxygen, sulfur and nitrogen. The remaining atoms of the ring are recognized as carbon atoms by those skilled in the art. Rings may be saturated or unsaturated. Examples of heterocycle groups include thiopheneyl, furyl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyrimidyl, pyrazinyl, pyridiazinyl, triazinyl, thiadiazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl or the like.

The term "substituted heterocycle" represents a heterocycle group substituted with one or moieties chosen from the group consisting of halogen, hydroxy, cyano, nitro, $C_1$–$C_6$ alkyl, $C_1$–$C_4$ alkoxy, alkoxycarbonyl, carboxy, carboxymethyl, hydroxymethyl, amino, aminomethyl or trifluoromethyl. Further, the heterocycle group can be optionally fused to one or two aryl groups to form a benzo-fused group. Examples of a substituted heterocycle include 1,2,3,4-tetrahydrodibenzofuranyl, 2-methylbenzylfuranyl and 3,5 dimethylisoxazolyl.

The term "alkoxycarbonyl" represents a carbonyl group having a $C_1$–$C_6$ alkyl group attached to the carbonyl carbon through an oxygen atom. Examples of this group include t-butoxycarbonyl, methoxycarbonyl, and the like.

The term "aryloxycarbonyl" represents a carbonyl group bearing an aryl group attached to the carbonyl carbon through an oxygen atom. Representatives of this group include phenoxycarbonyl, (4-chlorophenoxy) carbonyl, (3-nitrophenoxy)carbonyl, and the like.

All of the formula I compounds are believed to be antagonists of the AMPA receptors, and certain compounds are most preferred for such use. Preferably, $R^1$ and $R^2$ are hydrogen; $R^3$ is aryl, arylalkyl or thiophene; $R^4$ is tetrazole or COOH; and m and n are each 0 or 1. Representative compounds from this group of preferred compounds include: 6-(4-(1(2)H-tetrazol-5-yl)phenyl)-decahydroisoquinoline-3-carboxylic acid; 6-(4-carboxyphenyl)decahydroisoquinoline-3-carboxylic acid; 6-(5-(1(2)H-tetrazol-5-yl)thiophene-2-yl)decahydroisoquinoline-3 carboxylic acid; 6-(4-(1(2)H-tetrazol-5-yl)cyclohexyl)decahydroisoquinoline-3 carboxylic acid, and the like.

Some of the formula I compounds are most preferred for use as EAA receptor antagonists. These most preferred compounds define $R^3$ as phenyl, thiopheneyl, or cyclohexyl, and m and n are both 0. The remaining variable elements of the most preferred compounds are as defined in the preceding paragraph, with the most preferred structures as follows:

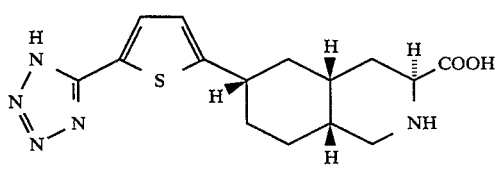

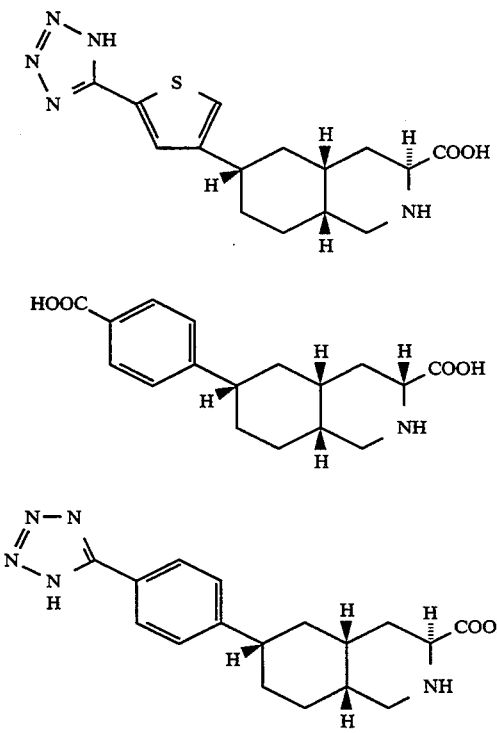

Representative compounds from this group of most preferred group of compounds are 6-(4-(1(2)H-tetrazol-5-yl)phenyl)decahydroisoquinoline-3-carboxylic acid; 6-(4-carboxyphenyl)decahydroisoquinoline-3-carboxylic acid; 6-(5-(1(2)H-tetrazol-5-yl)thiophene-2-yl)decahydroisoquinoline-3-carboxylic acid; 6-(4-(1(2)H-tetrazol-5-yl )cyclohexyl)decahydroisoquinoline-3-carboxylic acid, and the like.

The formula I compounds of the present invention have the relative stereochemistry as shown above. These compounds preferably possess at least four assymmetric carbon atoms. The asymmetric centers are the substituted carbon atom adjacent to the $NR^1$ group (C3), the carbon where $(CH_2)n$ is attached to the ring (C6), and the two bridge carbon atoms (C4a and C8a). As such, the preferred formula I compounds may exist as diastereomers each of which is a racemic mixture of the enantiomers. The compounds of the present invention include not only the racemates, but also their respective enantiomers. The preferred configuration amongst the possible diastereomers is 3SR,4aRS,6SR,-8aRS, and the preferred configuration for the enantiomer of this diastereomer is 3S,4aR,6S,8aR. The relative and absolute stereochemistry or this enantiomer is:

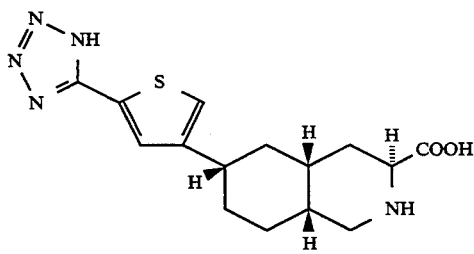

Ia

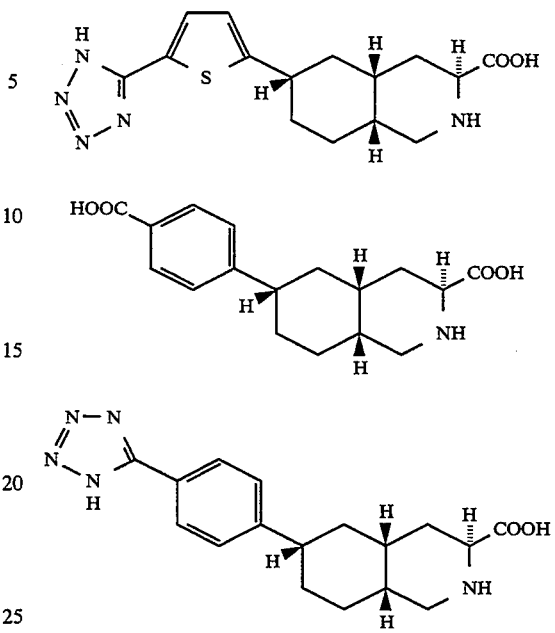

The compounds of this invention may include a tetrazole ring, which is known to exist as tautomeric structures, namely the 1H and 2H tautomers, which designate the position number of the nitrogen atom to which the hydrogen atom is bonded. The structures are as follow:

(1H)

(2H)

The mixture of tautomers is referred to as a 1(2)H-tetrazole. Since the two tautomers are in virtual equilibrium, the present invention contemplates the use of a combination of both tautomers as well as the individual tautomers.

The present invention includes the pharmaceutically acceptable salts of the compounds defined by formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I, wherein $R^1$ is hydrogen, $C_1$–$C_{16}$ alkyl, or arylalkyl. The alkali metal and alkaline earth metal salts are generally prepared by the reaction of the hydroxide form of the desired metal salt with a compound of formula I, wherein $R^2$ is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, ammonium, magnesium, tetramethylammonium potassium trimethylammonium, sodium, methylammonium, calcium, and the like salts.

The formula I compounds of the present invention may be chemically synthesized from a common intermediate, 6-oxodecahydroisoquinoline-3-carboxylate (VIII). A synthesis of this compound was described in U.S. Pat. No. 4,902,695, which is incorporated herein by reference. An improved synthesis of this intermediate from d,l-m-tyrosine is shown in Scheme I.

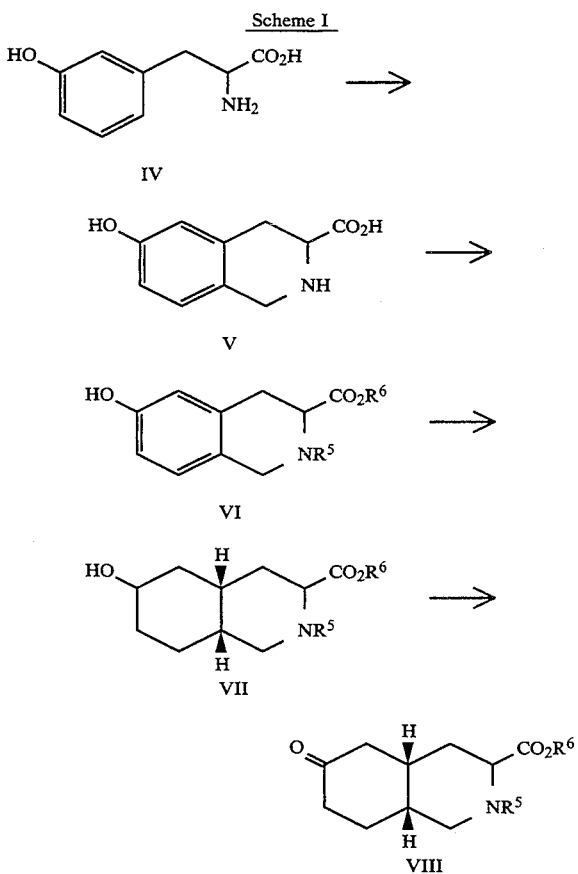

Scheme I

Generally, m-tyrosine (IV) is condensed with formaldehyde to form a 6-hydroxy substituted tetrahydroisoquinoline-3-carboxylic acid (V). This compound is esterified at the carboxyl group and blocked on the ring nitrogen with a suitable protecting group, to provide a doubly protected intermediate (VI). This intermediate is reduced to prepare the protected 6-hydroxydecahydroisoquinoline-3-carboxylate (VII). The 6hydroxyl group is then oxidized to a 6-oxo group to give common intermediate VIII.

More specifically, meta-tyrosine, preferably racemic m-tyrosine, is condensed with formaldehyde to form the hydroxy substituted tetrahydroisoquinoline-3-carboxylate (V). This reaction is preferably carried out in deionized water containing concentrated hydrochloric acid at a temperature of about 55° C. to about 70° C. for about 0.5 to about two hours. The formula V compound is preferably isolated by cooling the reaction mixture to a temperature of about 3° C. to about 10° C. and removing the product by filtration.

This compound is preferably protected on both the 3-carboxyl group and the ring nitrogen. Methods for the protection of amino groups and carboxyl groups are generally described in McOmie, Protective Groups in Organic Chemistry, Plenum Press, New York, 1973, and Greene and Wutz, Protecting Groups in Organic Synthesis, 2d. ed., John Wiley and Sons, New York,1991. The carboxyl group may be protected as the $C_1$–$C_6$ alkyl, substituted alkyl, or aryl ester. The preferred ester is the $C_1$–$C_6$ alkyl ester; the ethyl ester is the most preferred. This ester is prepared by the reaction of intermediate V with a mixture of ethanol and concentrated sulfuric acid. The reaction is preferably carried out at the reflux temperature of the solvent for a period of about 16 Hours. The ring nitrogen may be protected with an acyl or alkoxycarbonyl group. The preferred protecting groups are t-butoxycarbonyl and methoxycarbonyl. The most preferred protecting group is methoxycarbonyl.

The 2-methoxycarbonyl protecting group is added using standard synthetic organic techniques. The ethyl ester of intermediate V is reacted with methyl chloroformate in the presence of potassium carbonate to form intermediate VI. This reaction is preferably carried out at a temperature of about 0° C. to about 15° C. for a period of about two hours. Also, the reaction is preferably carried out by the subsequent addition of potassium carbonate and methyl chloroformate to the esterification reaction mixture. Intermediate VI, wherein $R^5$ is methoxycarbonyl and $R^6$ is ethyl, is preferably isolated by extraction and crystallization (ethanol/water)

Intermediate VII is prepared by reduction of intermediate VI. The preferred method of reduction is catalytic hydrogenation. Suitable catalysts include palladium on carbon, platinum on carbon, palladium on alumina, platinum oxide, ruthenium on alumina, rhodium on alumina, or rhodium on carbon. The preferred catalysts are ruthenium on alumina, rhodium on alumina, or rhodium on carbon. The most preferred catalyst for this reduction is rhodium on carbon. Suitable solvents for the reaction include polar organic solvents, such as ethyl acetate, methanol, and ethanol. Ethyl acetate ms the preferred solvent for the reaction. The reduction is carried out at a hydrogen pressure of about 100 psi to about 1000 psi and at a temperature of about 80° C. to about 150° C. when the reaction employs rhodium on alumina, the reaction is complete after about 24 hours. The catalyst may be removed by filtration and the protected 6-hydroxydecahydro-isoquinoline-3-carboxylate used in the next step without isolation.

The 6-hydroxy group of intermediate VII is oxidized to a 6-oxo group in the preparation of intermediate VIII. This transformation is preferably accomplished by the use of a mild oxidizing agent. Suitable mild oxidizing agents include sodium hypochlorite, ruthenium trichloride/sodium periodate, and ruthenium trichloride/periodic acid. Other oxidizing agents, such as pyridinium chlorochromate (PCC), Jones' reagent, dimethylsulfoxide/N-chlorosuccinimide, tetrapropylammonium perruthenate (TPAP), pyridine/$SO_3$, and hypochlorous acid, are also useful in effecting this transformation. Preferably, the filtered ethyl acetate solution containing intermediate VII is treated with ruthenium trichloride and water, and the resulting mixture cooled to a temperature of about −10° C. to about 25° C. The two-phase mixture is next treated with periodic acid. After the addition of periodic acid, the reaction mixture is allowed to warm to a temperature of about 20° C. to about 35° C. The desired product, intermediate VIII, is isolated using standard techniques.

Alternatively, intermediate VI is reduced to prepare intermediate VIII. The preferred method of reduction is catalytic hydrogenation. This reaction gives a mixture of 6-hydroxy intermediate VII and 6-keto intermediate VIII. Without further purification, this mixture can be used in a second step to oxidize the 6-hydroxy intermediate VII of the mixture to intermediate VIII using the reagents described in the previous paragraph. Suitable catalysts for the reduction step of this transformation include palladium on carbon and rhodium on carbon. The preferred catalyst is rhodium on carbon. Suitable solvents for this reaction include polar organic solvents, such as ethyl acetate, methanol, and ethanol. Ethyl acetate is a preferred solvent for the reaction. The reduction is carried out at a hydrogen pressure of about 30 psi to about 200 psi and at a temperature of about 70° C. to about 90° C. The preferred conditions for this transformation are a hydrogen pressure of about 100 psi and a temperature of about 85° C. When the reaction employs rhodium on carbon, the reaction is complete after about two hours to about 24 hours. The catalyst may be removed by filtration and the products used in the next step without further isolation.

The synthetic scheme described in the preceding paragraphs produces a mixture of diastereomers, whose relative configurations are illustrated by VIIIa and VIIIb.

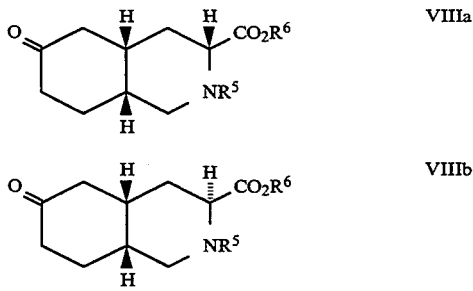

The predominant diastereomer from this scheme is intermediate VIIIa. This mixture of diastereomers may be equilibrated to a mixture where VIIIb is the predominant diastereomer by treatment with a strong base. Suitable strong bases for this equilibration include metal alkoxides, such as sodium ethoxide and potassium t-butoxide, and lithium diisopropylamide. The preferred strong base for the equilibration is sodium ethoxide. When a metal alkoxide is used as a base, the corresponding alcohol may be used as a solvent. The preferred solvent for the equilibration is ethanol. When sodium ethoxide and ethanol are used, the equilibration may be carried out at a temperature of about room temperature to about thee reflux temperature of the solvent. Preferably, the equilibration, when carried out in NaOEt/EtOH, is carried out at about 40° C. This equilibration requires from about one to about six hours. The preferred diastereomer, intermediate VIIIb, is isolated by crystallization from ether ($R^5$ is methoxycarbonyl and $R^6$ is ethyl).

The enantiomers of each diastereomeric pair of intermediate VIII are resolved using standard resolution techniques. See Jacques, Collet, and Wilen, Enantiomers, Racemates, and Resolutions, John Wiley and Sons, New York, 1981. The preferred method for resolution of the diastereomers and enantiomers uses chiral amines to form the diastereomeric salts. Suitable chiral amines are described in Jacques et al., Chapter 5, pages 253–259. Examples of suitable chiral amines include R-(+)-α-methylbenzylamine, S-(−)-α-methylbenzylamine, (−)-α-(2-naphthyl)ethylamine, yohimbine, (+)-amphetamine, (−)-ephedrine, strychnine, brucine, quinine, quinidine, cinchonine, cinchonidine, and the like. The preferred chiral amines are α-methylbenzylamine, brucine, quinine, quinidine, cinchonine, cinchonidine. The more preferred chiral amines are α-methylbenzylamine, brucine, and quinine. The most preferred chiral amine for the resolution of VIIIb is α-methylbenzylamine.

The preferred method of resolving the preferred enantiomer is described in the following. The ethyl ester, intermediate VIIIb where $R^5$ is methoxycarbonyl and $R^6$ is ethyl, is hydrolyzed using 5N sodium hydroxide at a temperature of about 5° C. to about 40° C. for a period of about 0.5 to about two hours. Suitable solvents for this transformation include the alcohols, such as methanol and ethanol. The free acid may be isolated by extraction with ethyl acetate. The free acid, preferably in ethyl acetate solution, is treated with R-(+)-α-methylbenzylamine at a temperature of about 25° C. to about 35° C. for a period of about 15 to about 60 minutes. Intermediate (−)-VIIIb ($R^6$ is hydrogen) precipitates from the reaction solution as the R-(+)-α-methylbenzylamine salt. The material is further purified by reslurrying in warm (45°–50° C.) ethyl acetate. In a similar manner, (+)-VIIIb is prepared using S-(−)-α-methylbenzylamine. The relative and absolute stereochemistry of the structures of these intermediates is shown below. Intermediate (−)-VIIIb is the preferred enantiomer.

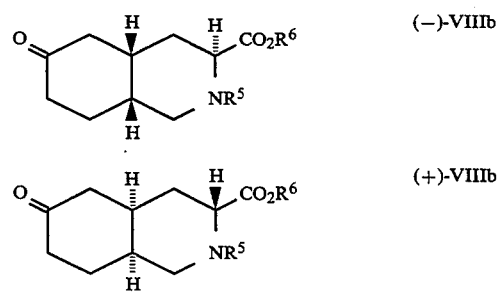

The resolved enantiomer is esterified on the 3-carboxyl group for further chemical modification. The preferred ester is the ethyl ester. Suitable esterification conditions include the reaction of intermediate VIII ($R^6$ is hydrogen) with an akylating reagent in the presence of a base. Suitable alkylating reagents for the present transformation include ethyl iodide, ethyl bromide, ethyl chloride, and diethyl sulfate. The base is selected from the group consisting of triethylamine, N,N-diisopropylethylamine, pyridine, collidine, sodium bicarbonate, and sodium carbonate. Suitable solvents for the esterification are polar organic solvents, such as dimethylformamide and acetonitrile. This esterification is preferably carried out using ethyl bromide and triethylamine in acetonitrile at the reflux temperature of the solvent for a period of about one to two hours.

The compounds of the present invention are chemically synthesized from common intermediate VIII by a number of different routes. When the synthesis begins with racemic intermediate VIII, the products are racemic. However, when the synthesis begins with intermediate (—)-VIIIb, the product is a single enantiomer. The specific synthetic steps of the routes described herein may be combined in other ways to prepare the formula I compounds. The following discussion is not intended to be limiting to the scope of the present invention, and should not be so construed.

The formula I compounds are prepared according to one of the following schemes. When $R^3$ is phenyl and $R^4$ is tetrazole the scheme is as follows:

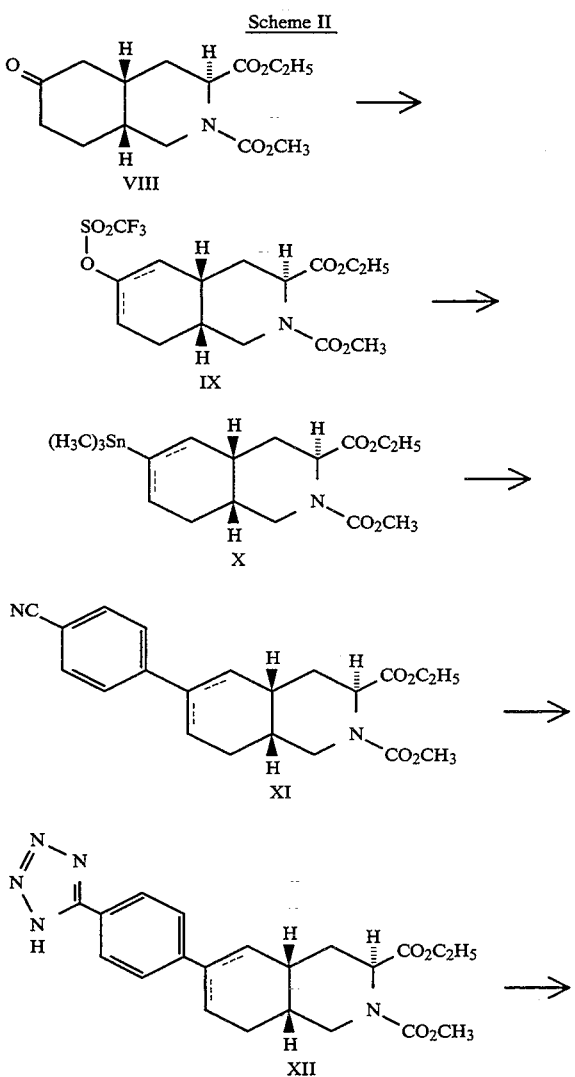

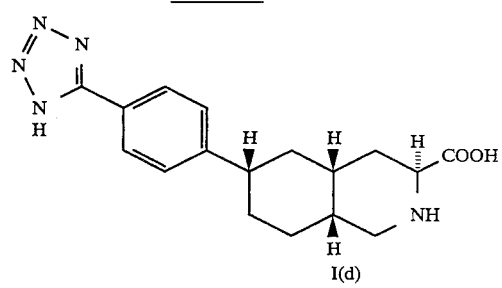

In Scheme II, intermediate VIII is reacted with N-phenyltriflimide ($PhN(SO_2CF_3)_2$) to, prepare enol triflate IX (as a mixture of regioisomers). This intermediate is converted to intermediate x (as a mixture of regioisomers) by reacting with hexamethyldistannane ($Me_3SnSnMe_3$) and tetrakis(triphenylphosphine)palladium(0). Intermediate X is reacted with a brominated benzonitrile and tetrakis(triphenylphosphine)palladium(0) to produce the intermediate XI (as a mixture of regioisomers). This intermediate is then reacted with tributyltin azide ($Bu_3SnN_3$) to produce the aryl-spaced tetrazole shown in intermediate XII (as a mixture of regioisomers). Finally, the double bond is reduced by hydrogenation, and the nitrogen and carboxy protecting groups are removed by hydrolysis to form the formula I(d) compound wherein $R^3$ is phenyl and $R^4$ is tetrazole. The exact procedures are listed in the examples which follow.

The general scheme for preparing compounds of Formula I(c) when $R^3$ is phenyl and $R^4$ is COOH are as follows:

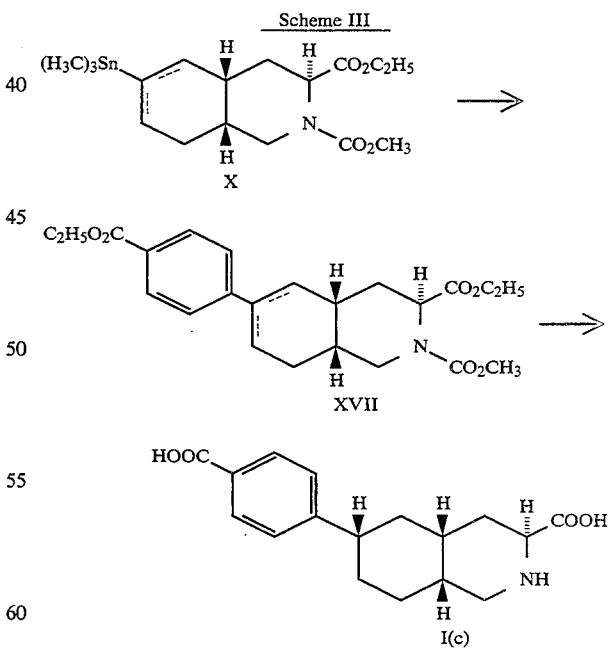

In this general scheme, intermediate X is reacted with a brominated benzoate ester to form the 6-benzoate substituted ring intermediate compound XVII (as a mixture of regioisomers). Hydrogenation and hydrolysis of intermediate XVII produces the compound designated by formula I(c) above wherein $R^3$ is phenyl and $R^4$ is —COOH. The exact procedure may be found in the later examples. A variation of scheme III may be used to produce compounds 1(e) and 1(f) shown below and described in detail in the later examples:

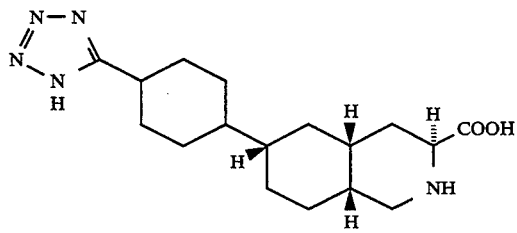

1(e)

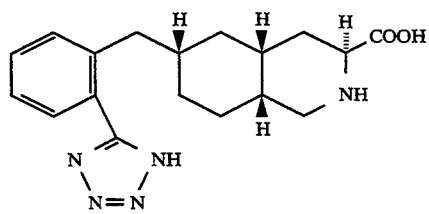

1(f)

The general scheme for preparing compounds of Formula I(a) and I(b) wherein $R^3$ is thiophene and $R^4$ is tetrazole are as follows:

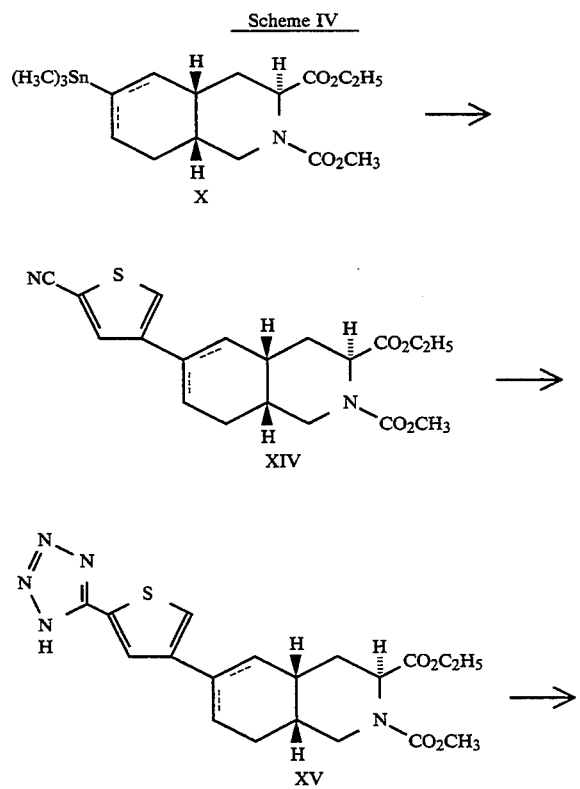

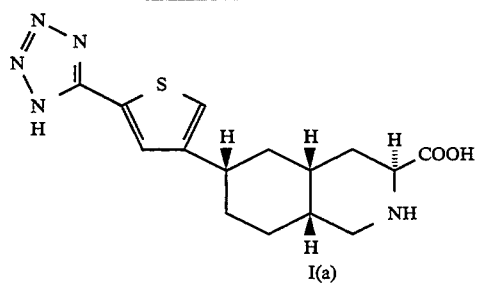

I(a)

In this general scheme, intermediate X is reacted with a brominated cyanothiophene to form the 6-(cyano)thiopheneyl substituted ring intermediate compound XIV (as a mixture of regioisomers). The intermediate is reacted with $Bu_3SnN_3$ to form the tetrazole-thiopheneyl substituted ring intermediate XV (as a mixture of regioisomers). Hydrogenation and hydrolysis of intermediate XV yields compound I(a) of formula I wherein $R^3$ is thiophene and $R^4$ is tetrazole The exact procedures for forming compounds I(a) and I(b) are described in the examples which follow.

Formula I compounds which include organic groupings in place of the preferred hydrogen atoms, and those which include other types of $R^3$ and $R^4$ substituents may be prepared by methods known to those skilled in the art.

The formula I compounds of the present invention are excitatory amino acid antagonists. In particular, these compounds are antagonists of the AMPA subtype of excitatory amino acid receptors. Therefore, another aspect of the present invention is a method of blocking the AMPA excitatory amino acid receptors in mammals which comprises administering to a mammal requiring decreased excitatory amino acid neurotransmission a pharmaceutically-effective amount of a compound of formula I.

The term "pharmaceutically-effective amount" is used herein to represent an amount of the compound of the invention which is capable of blocking the AMPA excitatory amino acid receptor. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, or intranasal routes. Alternatively, the compounds may be administered by continuous infusion. A typical daily dose will contain from about 0.01 mg/kg to about 30 mg/kg of the active compound of this invention. Preferred daily doses swill be about 0.05 mg/kg to about 24 mg/kg, more preferably about 0.1 to about 20 mg/kg.

A variety of physiological functions have been shown to be subject to influence by excessive or inappropriate stimulation of excitatory amino acid neurotransmission. The formula I compounds of the present invention are believed to have the ability to treat a variety of neurological disorders in mammals associated with this condition which include acute neurological disorders such as cerebral deficits subsequent to cardiac bypass surgery and grafting, stroke, cerebral ischemia, spinal cord trauma, head trauma, perinatal hypoxia, cardiac arrest and hypoglycemic neuronal damage. The formula I compounds are believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of a compound of formula I.

The formula I compounds of the present invention are also believed to have the ability to treat a variety of other neurological disorders in mammals that are associated with glutamate dysfunction including muscular spasms, convulsions, migraine headaches, urinary incontinence, psychosis, drug tolerance and withdrawal, anxiety, emesis, brain edema, chronic pain, and tardive dyskinesia. The formula I compounds are also useful as analgesic agents. Therefore, the present invention also provides methods for treating these disorders which comprise administering to a patient in need thereof an effective amount of a compound of formula I.

Experiments were performed to demonstrate the inhibitory activity of the formula I compounds of this invention at the α-amino-3-hydroxy-5-methylisoxazole-4-propionic acid (AMPA) subtype of excitatory amino acid receptors. The formula I compounds were tested for their ability to inhibit NMDA, AMPA, and kainic acid receptor binding to rat membranes in a radioligand binding assay using [$^3$H]CGS19755, [$^3$H]AMPA, and [$^3$H]KA. For all radioligand binding assays, male Sprague-Dawley rats were used. Displacement of the specific binding of [$^3$H]CGS19755 (10 nM) to Triton-X-treated synaptosomal membranes of rat forebrain was used to determine NMDA receptor affinity. Non-specific binding was determined using 10 μML-glutamate. Samples were incubated in an ice-bath for 30 minutes, and bound ligand was separated from the free ligand by rapid filtration through WHATMAN GF/B glass fiber filters. Murphy et al, *British J. Pharmacol.*, 95, 932–938 (1988). Kainate binding was performed using washed synaptosomal membranes from the rat forebrain as described by Simon et al, *J. Neurochem.*, 26, 141–147 (1976). Tritiated kainate (5 nM) was added to 50 mM Tris-HCl buffer (pH 7.4 at 4° C.) containing 200–300 μg/ml of tissue protein. Samples were incubated for 30 minutes in an ice-bath, then rapidly filtered using a Brandel cell harvester and WHATMAN GF/C filters. Filters were washed twice with 3 ml of cold buffer. Non-specific binding was determined using 100 μM non-labeled kainate. The binding of [$^3$H]AMPA (5 nM) was conducted with crude membranes of rat forebrain in the presence of 100 mM KSCN as described by Nielson et al., *Eur. J. Med. Chem. Chim. Ther.*, 21, 433–437 (1986). Non-specific binding was determined with 10 μM non-labeled AMPA. The concentration of the formula I compound that inhibited 50% binding (IC$_{50}$, mean±standard error, n=3) as calculated by linear regression of displacement data transformed to the Hill equation as described by Bennett. Bennett, Neurotransmitter Receptor Binding, 57–90 (1978). The results of the radioligand binding assays are shown in Table I (all compounds are racemates, unless otherwise listed).

TABLE I

| (Receptor binding affinities) | | |
|---|---|---|
| Compound | Receptor | IC$_{50}$ (μM) |
| I(a) | NMDA | 17.4 |

TABLE I-continued

| (Receptor binding affinities) | | |
|---|---|---|
| Compound | Receptor | IC$_{50}$ (μM) |
| I(a) | AMPA | 4.3 |
| I(a) | KA | 53.7 |
| I(b) | NMDA | >50 |
| I(b) | AMPA | 4.3 |
| I(b) | KA | >100 |
| I(c) | NMDA | >100 |
| I(c) | AMPA | 6.1 |
| I(c) | KA | >100 |
| I(d) | NMDA | 84.2 |
| I(d) | AMPA | 3.2 ± 0.5 |
| (−)-I(d) | AMPA | 1.3 |
| (+)-I(d) | AMPA | 55.4 |
| I(d) | KA | — |
| I(e) | NMDA | >100 |
| I(e) | AMPA | 7.0 |
| I(e) | KA | >100 |
| I(f) | NMDA | >100 |
| I(f) | AMPA | 46.8 |
| I(f) | KA | 17.6 |

TABLE II

| (Cortical Wedge Electrophysiology, to distinguish antagonist activity versus the agonist shown) | | |
|---|---|---|
| Compound | Agonist | IC$_{50}$ (μM) |
| I(a) | AMPA | 27.3 ± 2.4 |
| I(b) | AMPA | 43.3 ± 8.6 |
| I(c) | AMPA | 15.0 ± 2.0 |
| I(d) | AMPA | 14.9 ± 2.1 |
| (−)-I(d) | AMPA | 13.4 ± 1.8 |
| (+)-I(d) | AMPA | 58.7 ± 17.4 |
| I(e) | AMPA | 17.7 ± 2.7 |
| I(f) | AMPA | >100 |
| I(f) | KA | 14.5 ± 2.7 |

The data shows that the formula I compounds possess selective affinity for the AMPA ionotropic glutamate receptors. The radioligand binding assay is the preferred assay for discriminating between AMPA and KA receptor selectivity. All of the formula I compounds displaced $^3$H-AMPA and with IC$_{50}$ values less than 10 μM (Table I). The cortical wedge assay is the preferred assay for discriminating between AMPA and NMDA receptor selectivity (Table II). This assay which is well known and documented in the prior art also distinguishes between agonist and antagonist activity. All of the formula I compounds, in particular compound I(a), are shown to be AMPA receptor antagonists. Compound I(f) is also a kainic acid receptor antagonist.

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium sterate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 to about 5000 mg, more preferably about 25 to about 3000 mg of the active ingredient. The most preferred unit dosage form contains about 100 to about 2000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1
Hard gelatin capsules are prepared using the following ingredients:

| | Quantity (mg/capsule) |
|---|---|
| 6-(4-(1(2)H-Tetrazol-5-yl)phenyl)-decahydroisoquinoline-3-carboxylic acid | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| 6-(4-(1(2)H-Tetrazol-5-yl)phenyl)-decahydroisoquinoline-3-carboxylic acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| 6-(5-(3-Hydroxyisoxazol-5-yl)thiophen-2-yl)-decahydroisoquinoline-3-carboxylic acid | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredients are made as follows:

| | |
|---|---|
| 6-(5-(3-Hydroxyisoxazol-5-yl)thiophen-2-yl)-decahydroisoquinoline-3-carboxylic acid | 60 mg |
| Starch | 45 mg |
| microcrystalline cellulose | 35 mg |
| Polyvinylpyrrolidone | 4 mg |
| Sodium carboxymethyl starch | 4.5 mg |
| magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| 6-(4-(1(2)H-Tetrazol-5-yl)cyclohexyl)-decahydroisoquinoline-3-carboxylic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| 6-(5-(1(2)H Tetrazol-5-yl)thiophene-2-yl)decahydro-isoquinoline-3-carboxylic acid | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 7 Suspensions each containing 50 mg of medicament per 5 ml dose are made as follows: | |
|---|---|
| 6-(4-(1(2)H-Tetrazol-5-yl)phenyl)decahydroisoquinoline-3-carboxylic acid | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

| Formulation 8 An intravenous formulation may be prepared as follows: | |
|---|---|
| 6-(5-(1(2)H-Tetrazol-5-yl)thiophene-3-yl)-decahydroisoquinoline-3-carboxylic acid | 100 mg |
| Mannitol | 100 mg |
| 5N Sodium hydroxide | 200 μl |
| Purified water to total | 5 ml |

The following specific examples are indicative of synthesizing procedures which are used in producing compounds of this invention.

General Experimental:

All experiments were run under a positive pressure of dry nitrogen. Tetrahydrofuran (THF) was distilled from sodium prior to use. All other solvents and reagents were used as obtained. Thin layer chromatography was performed using E. Merck Kieselgel 60 $F_{254}$ plates, 5×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). "Chromatography" refers to flash chromatography, which was performed as described by Still, et al. (Still, W. C.; Kahn, M.; Mitra, A. *J. Org. Chem.* 1978, 43, 2923). Elemental analyses for carbon, hydrogen and nitrogen were determined on a Control Equipment Corporation 440 Elemental Analyzer. Melting points were determined in open glass capillaries on a Gallenkamp hot air bath melting point apparatus, and are uncorrected.

EXAMPLE I

Preparation of 3SR,4aRS,6SR,8aRS-6-(5-(1(2)H-tetrazol-5-yl)thiophene-3-yl) decahydroisoquinoline-3-carboxylic acid A. To a −78° C. solution of 100 mL of lithium bis(-trimethylsilyl)amide in 230 mL of THF was added 25.8 g of ethyl 2-methoxycarbonyl-6-oxodecahydroisoquinoline-3-carboxylate in 45 mL of THF, and the mixture stirred at this temperature for 1 hr. 32.5 g of N-phenyltriflimide was added to this solution, which was then warmed to room temperature and stirred for 3 hr. The reaction was diluted with 400 mL of ether and washed with 400 mL of 10% aqueous sodium bisulfate. The aqueous layer was extracted with 3×200 mL of ether, then the combined organics were dried (MgSO$_4$), filtered and concentrated in vacuo. Preparative HPLC (gradient elution with hexane to 35% ethyl acetate/hexane) afforded 31.2 g (83%) of $\Delta^{5,6}/\Delta^{6,7}$ ethyl 6-((trifluoromethanesulfonyl)oxy)-2-methoxycarbonyloctahydroisoquinoline-3-carboxylate.

Analysis calculated for $C_{15}H_{20}F_3NO_7S$: C, 43.37; H, 4.85; N, 3.37. Found: C, 43.44; H, 4.89; N, 3.35.

B. To a solution of 11.0 g of the intermediate from example 1A, 3.5 g of lithium chloride and 10.0 g of hexamethyldistannane in 180 mL of THF, which was degassed by bubbling nitrogen through the solution for 15 min, was added 1.6 g of tetrakis(triphenylphosphine)palladium(0). The solution was heated to reflux for 1 hr, then cooled, diluted with 180 mL of ether, filtered through diatomaceous earth and the filtrate concentrated in vacuo. Chromatography (600 g of silica gel, 25% ethyl acetate/hexane as eluent) afforded 9.4 g (79%) of $\Delta^{5,6}/\Delta^{6,7}$ ethyl 6-(trimethylstannyl)-2-methoxycarbonyloctahydroisoquinoline-3-carboxylate.

Analysis calculated for $C_{17}H_{29}NO_4Sn$: C, 47.47; H, 6.80; N, 3.26. Found: C, 47.56; H, 6.58; N, 3.36.

C. A mixture of 4.5 g of the intermediate from example 1B, 2.0 g of 3-bromo-5-cyanothiophene and 0.6 g of tetrakis(triphenylphosphine)palladium(0) in 60 mL of xylene was degassed by bubbling nitrogen through the solution for 15 min, then heated to reflux overnight. The reaction was cooled and diluted with 60 mL of dichloromethane. Chromatography (200 g of silica gel, 25% ethyl acetate/hexane as eluent) gave 1.6 g (40%) of $\Delta^{5,6}/\Delta^{6,7}$ ethyl 6-(5-cyanothiophene-3-yl)-2-methoxycarbonyloctahydroisoquinoline-3-carboxylate.

Analysis calculated for $C_{19}H_{22}N_2O_4S$: C, 62.37; H, 6.47; N, 21.39. Found: C, 61.20; H, 6.46; N, 20.40.

D. 1.5 g of the intermediate from example 1C was combined with 2.7 grams of azidotri-n-butylstannane and heated to 80° C. for 3 days. The reaction was cooled and diluted with 100 ml of ether. To this solution was added 100 ml of ether which had HCl gas bubbled through for 5 minutes, then the mixture concentrated in vacuo The residue was dissolved 100 ml of acetonitrile, extracted with six 50 ml portions Of hexane, and the acetonitrile layer concentrated in vacuo. Chromatography (100 g of silica gel, 2% acetic acid/50% ethyl acetate/hexane as eluent) gave 1.3 g (78%) of $\Delta^{5,6}/\Delta^{6,7}$ ethyl 6-(5-(1(2)H-tetrazol-5-yl)thiophene-3-yl)-2 -methoxycarbonyloctahydroisoquinoline-3-carboxylate.

Analysis calculated for $C_{19}H_{23}N_5O_4N$: C, 54.66; H, 5.55; N, 16.77. found: C, 54.44; H, 5.79; N, 16.53.

E. 1.3 g of the intermediate from example 1D in 50 ml of ethanol was hydrogenated with 1.3 p of 5% Pd/C at 40° C. and 60 psi for 6 hr, then cooled, filtered through diatomaceous earth and the filtrate concentrated in vacuo. The residue was dissolved in ethyl acetate, filtered through diatomaceous earth and the filtrate again concentrated in vacuo to afford 0.3 g (24%) of ethyl 6-(5-(1(2)H-tetrazol-5-yl)thiophene-3-yl)-2-methoxycarbonyldecahydroisoquinoline-3-carboxylate.

F. 0.3 g of the intermediate from example 1E was heated to 100 °C. overnight in 50 mL of 6N aqueous hydrochloric acid, then cooled and concentrated in vacuo. Ion exchange chromatography (Dowex 50-X8, 10% pyridine/water as eluent) afforded 0.1 g (47%) of the title compound.

m.p. 306 ° C. (dec.)

Analysis calculated for $C_{15}H_{19}N_5O_2S \cdot 0.25\ H_2O$: C, 53.32; H, 5.82; N, 21.00. Found: C; 53.25; H, 5.79; N, 20.60.

EXAMPLE 2

Preparation of 3SR,4aRS,6SR,8aRS-6-(5-(1(2)H-tetrazol-5-yl)thiophene-2-yl) decahydroisoquinoline-3-carboxylic acid A. A mixture of 5.9 g of the intermediate from example 1B, 2.6 g of 2-bromo-5-cyanothiophene and 0.8 g of tetrakis(triphenylphosphine)palladium(0) in 60 mL of xylene was degassed by bubbling nitrogen through the solution for 15 min, then heated to reflux for 2 hr. The reaction was cooled and diluted with 60 mL of dichloromethane. Chromatography (200 g of silica gel, 25% ethyl acetate/hexane as eluent) gave 2.7 g (51%) of $\Delta^{5,6}/\Delta^{6,7}$ ethyl 6-(5-cyanothiophene-2-yl)-2-methoxycarbonyloctahydroisoquinoline-3-carboxylate.

Analysis calculated for $C_{19}H_{22}N_2O_4S$: C, 60.94; H, 5.92; N, 7.48. Found: C, 60.72; H, 6.00; N, 7.38.

B. As for example 1D, 2.0 g of intermediate 2A and 3.5 g of azidotri-n-butylstannane gave 1.0 g of $\Delta^{5,6}/\Delta^{6,7}$ ethyl 6-(5(1(2)H-tetrazol-5-yl)thiophene-2-yl)-2-methoxycarbonyloctahydroisoquinoline-3-carboxylate.

Analysis calculated for $C_{19}H_{25}N_5O_4S$: C, 54.66; H, 5.55; N, 6.77. Found: C, 54.07; H, 5.62; N, 16.43.

C. 1.0 g of intermediate 2B were hydrogenated as per example 1E to yield 0.6 g (62%) of ethyl 6-(5-(1(2)H-tetrazol-5-yl)thiophene-2-yl)-2-methoxycarbonyldecahydroisoquinoline-3carboxylate.

D. As per example 1F, hydrolysis of 0.6 g of intermediate 2C afforded 0.2 g (43%) of the title compound.
m.p. 228 ° C. (dec.)

Analysis of $C_{15}H_{19}N_5O_2S \cdot 0.25\ H_2O \cdot HCl$-Calculated: C-48.12, H-5.25, N-18.71; Found: C-48.07, H-5.71, N-18.70.

EXAMPLE 3

Preparation of 3SR,4aRS,6SR,8aRS-6-(4-carboxyphenyl) decahydroisoquinoline-3-carboxylic acid.

A. A mixture of 4.0 g of the intermediate from example 1B, 2.1 g of ethyl 4-bromobenzoate and 0.5 g of tetrakis(triphenylphosphine)palladium(0) in 60 mL of xylene was degassed by bubbling nitrogen through the solution for 15 min, then heated to reflux for 2 hr. The reaction was cooled and diluted with 60 mL of dichloromethane. Chromatography (200 g of silica gel, 25% ethyl acetate/hexane as eluent) gave 1.9 g (50%) of $\Delta^{5,6}/\Delta^{6,7}$ ethyl 6-(4-carbethoxyphenyl)-2-methoxycarbonyloctahydroisoquinoline-3-carboxylate.

Analysis calculated for $C_{23}H_{29}NO_6$: C, 66.49; H, 7.04; N, 3.37. Found: C, 66.37; H, 7.09; N, 3.31.

B. 1.8 g of intermediate 3A was hydrogenated as per example 1E to yield 1.2 g (65%) of ethyl 6-(4-carbethoxyphenyl)-2-methoxycarbonyldecahydroisoquinoline-3-carboxylate.

C. 1.1 g of intermediate 3B was hydrolyzed by heating overnight at reflux in 50 mL of 6N aqueous hydrochloric acid. The mixture was cooled, and the precipitate that formed was filtered and washed with water, acetone and ether to afford 0.5 g (59%) of the title compound.
m.p. 336 ° C. (dec.)

Analysis calculated for $C_{17}H_{21}NO_4 \cdot HCl$: C, 60.09; H, 6.52; N, 4.12. Found: C, 60.17; H, 6.60; N, 4.40.

EXAMPLE 4

Preparation of 3SR,4aRS,6SR,8aRS-6-(4-(1(2)H-tetrazol-5-yl)phenyl)-decahydroisoquinoline-3-carboxylic acid A. A mixture of 4.0 g of the intermediate from example 1B, 1.7 g of 4-bromobenzonitrile and 0.5 g of tetrakis(triphenylphosphine)palladium(0) in 60 mL of xylene was degassed by bubbling nitrogen through the solution for 15 min, then heated to reflux for 2 hr. The reaction was cooled and diluted with 60 mL of dichloromethane. Chromatography (200 g of silica gel, 25% ethyl acetate/hexane as eluent) gave 1.9 g (55%) of $\Delta^{5,6}/\Delta^{6,7}$ ethyl 6-(4-cyanophenyl)-2-methoxycarbonyloctahydroisoquinoline-3-carboxylate.

Analysis calculated for $C_{21}H_{24}N_2O_4$: C, 68.46; H, 6.57; N, 7.60. Found: C, 68.33; H, 6.46; N, 7.46.

B. As for example 1D, 2.0 g of intermediate 4A and 3.5 g of azidotri-n-butylstannane gave 1.7 g (77%) of $\Delta^{5,6}/\Delta^{6,7}$ ethyl 6-(4-(1(2)H-tetrazol-5-yl)phenyl)-2-methoxycarbonyloctahydroisoquinoline-3-carboxylate.

Analysis calculated for $C_{21}H_{25}N_5O_4$: C 61.30; H, 6 12; N 17.02. Found: C, 61.02; H, 6.24; N, 17.28.

C. 1.7 g of intermediate 4B was hydrogenated as per example 1E to yield 0.9 g (50%) of ethyl 6-(4-1(2)H-tetrazol-5-yl))-2-methoxycarbonyldecahydroisoquinoline-3-carboxylate.

Analysis calculated for $C_{21}H_{27}N_5O_4$: C, 61.00; H, 6.58; N, 16.94. Found: C, 60.91; H, 6.59; N, 16.80.

D. 0.9 g of intermediate 4C was hydrolyzed as per example 3C to afford 0.5 g (70%) of the title compound.
m.p >350 ° C.

Analysis calculated for $C_{17}H_{21}N_5O_2$: C, 61.52; H, 6.53; N, 21.10. Found: C, 61.59; H, 6.62; N, 21.14.

E. The reagent from example 1A was prepared using either the (−)-3S,4aR,8aR-ketone VIIIa or the (+)-3R,4aS,8aS-ketone VIIIb, and this material was transformed as in Examples 4A, 4B, 4C and 4D to afford the (−)-3S,4aR,6S,8aR and the (+)-3R,4aS,6R,8aS isomers of the title compound.

(−) -3S,4aR, 6S,8aR-isomer:

Analysis calculated for $C_{17}H_{21}N_5O_2 \cdot HCl \cdot 0.25\ H_2O$: C, 55.43; H, 6.16; N, 19.01. Found: C, 55.33; H, 6.00; N, 19.18. $[\alpha]_D = -84.0°$ (c=1, 1N HCl).

(+)-3R,4aS,6R,8aS-isomer:

Analysis calculated for $C_{17}H_{21}N_5O_2 \cdot 1.25\ H_2O$: C, 58.36; H, 6.77; N, 20.01. Found: C, 58.25; H, 6.33; N, 20.76. $[\alpha]_D = +24.8°$ (c=1, 1N HCl)

EXAMPLE 5

Preparation of 3SR, 4aRS,6SR, 8aRS-6-(4-(1(2)H-tetrazol-5-yl)cyclohex-1-1-yl)decahydroisoquinoline-3-carboxylic acid (compound 1 (e))

A. 1.7 g of intermediate 4A was stirred overnight at room temperature with 14 mL of 1N sodium hydroxide in 28 mL of absolute ethanol, then concentrated in vacuo. The residue was dissolved in 20 mL of water and extracted twice with 20 mL of ethyl acetate and twice with 20 mL of hexane. The aqueous phase was acidified to pH 1 with 5N aqueous hydrochloric acid, the resultant solid was filtered then redissolved in 50 mL of ethyl acetate, dried over $MgSO_4$, filtered and concentrated in vacuo to afford 1.4 g of $\Delta^{5,6}/\Delta^{6,7}$ 6-(4-cyanophenyl)-2-methoxycarbonyloctahydroisoquinoline-3-carboxylic acid.

B. As per example 1D, 1.4 g of intermediate 5A and 2.7 g of azidotri-n-butylstannane gave 0.8 (52%) of $\Delta^{5,6}/\Delta^{6,7}$ 6-(4-(1(2)H-tetrazol-5-yl)phenyl)-2-methoxycarbonyloctahydroisoquinoline-3-carboxylic acid.

C. 0.8 g of intermediate 5B was hydrogenated with 0.8 g of PtO$_2$ in 50 mL of ethanol at 40 ° C. and 60 psi overnight. The mixture was filtered through diatomaceous earth and concentrated in vacuo to afford 0.7 g (82%) of 6-(4-(1(2)H-tetrazol-5-yl)cyclohex-1-yl)-2-methoxycarbonyloctahydroisoquinoline-3-carboxylic acid.

D. 0.7 g of intermediate 5C was heated to reflux for 4 hr with 1.3 mL of iodotrimethylsilane in 6 mL of acetonitrile, stirred overnight at room temperature, then concentrated in vacuo. The residue was dissolved in 20 mL of Water and extracted 5 times with 20 mL of ether. The aqueous phase was concentrated in vacuo, and ion exchange chromatography (Dowex 50-X8, 10% pyridine/water as eluent) afforded a solid. This was suspended in 25 mL of acetone and heated to reflux for 1 hr, then filtered, washed with acetone and ether and dried in vacuo at 60 ° C. to afford 0.13 g (22%) of the title compound.

Analysis calculated for C$_{17}$H$_{29}$N$_5$O$_2$.1.8 H$_2$O.0.2 C$_3$H$_6$O: C, 56.00; H, 8.49; N, 18.55. Found: C, 56.29; H, 8.28; N, 18.17.

EXAMPLE 6

Preparation of 3SR,4aRS, 6SR,8aRS-6-(2-((1(2)H-tetrazol-5-yl)phenylmethyl)-decahydroisoquinoline-3-carboxylic acid (compound 1 (f))

A. 4.5 g of 2-diethylphosphonomethylbenzonitrile and 17.6 mL of a 1.0M solution of sodium bis(trimethylsilyl)amide in THF in 17 mL of THF was stirred 15 min at −78 ° C., then treated with 3.6 g of ethyl 2-methoxycarbonyl-6-oxodecahydroisoquinoline-3-carboxylate. After 15 min more at −78 ° C., the mixture was partitioned between ether (30 mL) and water (50 mL), the organic layer separated and the aqueous layer extracted with ether (3×30 mL). The combined organics were dried (MgSO$_4$), filtered and concentrated in vacuo. Chromatography (200 g of silica gel, 30% ethyl acetate/hexane as eluent) afforded 4.3 g (89%) of a mixture of E and Z ethyl 6-(2-(cyanophenyl)methylidine)-2-methoxycarbonyldecahydroisoquinoline -3-carboxylate.

Analysis calculated for C$_{22}$H$_{26}$N$_2$O$_4$: C, 69.09; H, 6.85; 7.32. Found: C, 69.05; H, 7.06; N, 7.37.

B. 4.2 g of the intermediate from Example 6A was hydrogenated overnight in 150 mL of ethanol with 0.8 g of 5% Pd/C at room temperature and 15 psi. Filtration through diatomaceous earth and concentration of the filtrate in vacuo afforded 3.4 g (80%) of ethyl 6-(2-(cyanophenyl)methyl)-2-methoxycarbonyldecahydroisoquinoline -3-carboxylate.

Analysis calculated for C$_{22}$H$_{28}$N$_2$O$_4$: C, 68.73; H, 7.34; N, 7.29. Found: C, 68.97; H, 7.23; N, 7.22.

C. As per example 1D, 1.7 g of intermediate 6B and 2.9 g of azidotri-n-butylstannane gave 0.8 g (56%) of ethyl 6-(2-((1(2)H-tetrazol-5-yl)phenyl)methyl)-2-methoxycarbonyldecahydroisoquinoline-3-carboxylate.

D. As per example 1E, 0.8 g of the intermediate from Example 6C afforded 0.5 g (78%) of the title compound.

m.p. >260 ° C. (dec.)

Analysis calculated for C$_{18}$H$_{23}$N$_5$O$_2$.0.5 H$_2$O: C, 61.70; H, 6.90; N, 19.89. Found: C; 61.50; H, 6.78; N, 19.63.

I claim:
1. A compound of the formula:

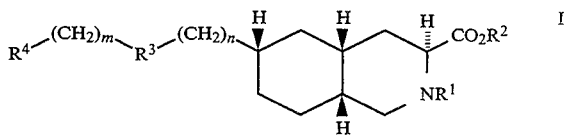

wherein:
wherein R$^1$ is H, C$_1$–C$_{10}$ alkyl, arylalkyl, alkoxycarbonyl, aryloxycarbonyl, or acyl;

R$^2$ is H, C$_1$–C$_6$ alkyl, substituted alkyl, C$_4$–C$_7$ cycloalkyl, or arylalkyl;

R$^3$ is aryl, arylalkyl, heterocycle, substituted heterocycle, cycloalkyl or cycloalkenyl;

R$^4$ is C$_2$H, S$_3$H, PO$_3$H$_2$, or one of the following cyclic groups:

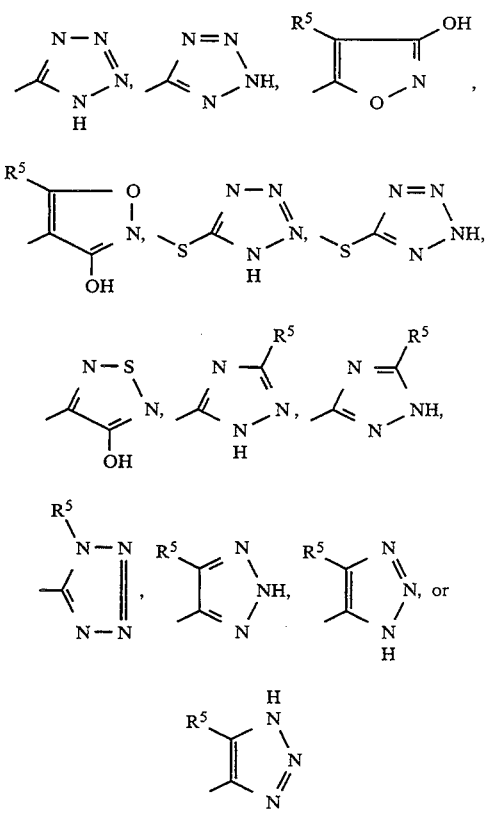

wherein
R$^5$ is H, C$_1$–C$_6$ alkyl or aryl;
m=0, 1 or 2; and
n=0, 1 or 2;
or a pharmaceutically acceptable salt thereof.

2. A compound of claim 1 wherein: n is 0 or 1, and m is 0 or 1.

3. A compound of claim 2 wherein: n is 0 and m is 0.

4. A compound of claim 3 wherein R$^3$ is thiophene or a substituted thiophene.

5. A compound of claim 4 wherein R$^4$ is tetrazole.

6. A compound of claim 3 wherein R$^3$ is phenyl or substituted phenyl.

7. A compound of claim 6 wherein R$^4$ is —COOH.

8. The compound of claim 3 wherein is R$^3$ is C$_4$–C$_7$ cycloalkyl, and R$^4$ is tetrazole.

9. The compound of claim 1 of the formula:

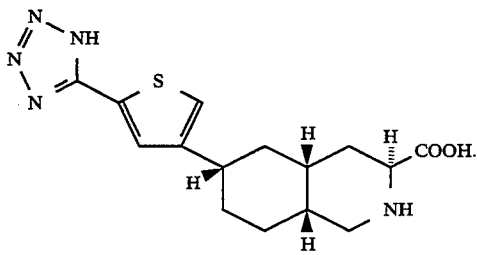

Ia

10. The compound of claim 1 of the formula:

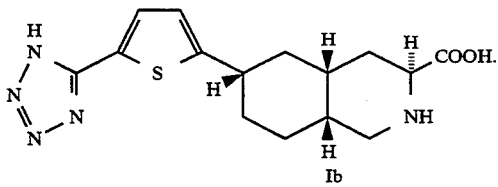

Ib

11. The compound of claim 1 of the formula:

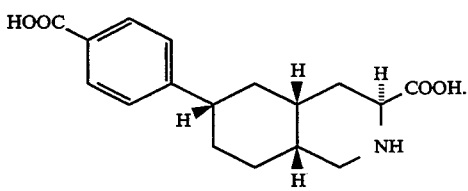

Ic

12. The compound of claim 1 of the formula:

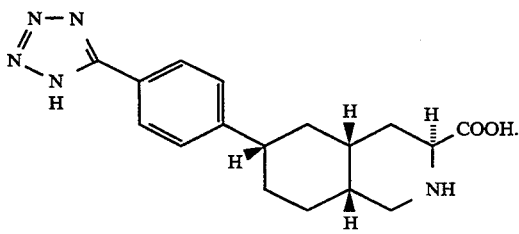

Id

13. A method of treating epilepsy in mammals comprising administration to a mammal requiring treatment for epilepsy an effective amount of a compound of claim 1.

14. A method of treating stroke in mammals comprising administration to a mammal requiring treatment for stroke an effective amount of a compound of claim 1.

15. A method of treating anxiety in mammals comprising administration to a mammal requiring treatment for anxiety an effective amount of a compound of claim 1.

16. A method of treating cerebral ischemia in mammals comprising administration to a mammal requiring treatment for cerebral ischemia an effective amount of a compound of claim 1.

17. A method of treating muscle spasms in mammals comprising administration to a mammal requiring treatment for muscle spasms an effective amount of a compound of claim 1.

18. A method of treating Huntington's Disease in mammals comprising administration to a mammal requiring treatment for Huntington's Disease an effective amount of a compound of claim 1.

19. A method of treating neurodegenerative disease in mammals comprising administration to a mammal requiring treatment for neurodegenerative disease an effective amount of a compound of claim 1.

20. A method of treating amyotrophic lateral sclerosis in mammals comprising administration to a mammal requiring treatment for amyotrophic lateral sclerosis an effective amount of a compound of claim 1.

21. A method of treating neural trauma in mammals comprising administration to a mammal requiring treatment for neural trauma an effective amount of a compound of claim 1.

22. A method of treating cerebral deficits in mammals comprising administration to a mammal requiring treatment for cerebral deficits an effective amount of a compound of claim 1.

23. A method of treating cognitive disorders in mammals comprising administration to a mammal requiring treatment for cognitive disorders an effective amount of a compound of claim 1.

24. A method of treating Parkinson's Disease in mammals comprising administration to a mammal requiring treatment for Parkinson's Disease an effective amount of a compound of claim 1.

25. A method of treating dementia in mammals comprising administration to a mammal requiring treatment for dementia an effective amount of a compound of claim 1.

26. A method of treating ocular damage in mammals comprising administration to a mammal requiring treatment for ocular damage an effective amount of a compound of claim 1.

27. A method of treating retinopathy in mammals comprising administration to a mammal requiring treatment for retinopathy an effective amount of a compound of claim 1.

28. A method of treating convulsions in mammals comprising administration to a mammal requiring treatment for convulsions an effective amount of a compound of claim 1.

29. A method of treating headaches in mammals comprising administration to a mammal requiring treatment for headaches an effective amount of a compound of claim 1.

30. A method of treating urinary incontinence in mammals comprising administration to a mammal requiring treatment for urinary incontinence an effective amount of a compound of claim 1.

31. A method of treating psychosis in mammals comprising administration to a mammal requiring treatment for psychosis an effective amount of a compound of claim 1.

32. A method of treating drug withdrawal in mammals comprising administration to a mammal requiring treatment for drug withdrawal an effective amount of a compound of claim 1.

33. A method of treating brain edema in mammals comprising administration to a mammal requiring treatment for brain edema an effective amount of a compound of claim 1.

34. A pharmaceutical formulation comprising an effective amount of a compound of claim 1 and a pharmaceutically accepted carrier, diluent, or excipient thereof.

35. A pharmaceutical formulation comprising an effective amount of a compound of claim 9 and a pharmaceutically accepted carrier, diluent, or excipient thereof.

36. A pharmaceutical formulation comprising an effective amount of a compound of claim 10 and a pharmaceutically accepted carrier, diluent, or excipient thereof.

37. A pharmaceutical formulation comprising an effective amount of a compound of claim 11 and a pharmaceutically accepted carrier, diluent, or excipient thereof.

38. A pharmaceutical formulation comprising an effective amount of a compound of claim 12 and a pharmaceutically accepted carrier, diluent, or excipient thereof.

39. The compound of claim 1 of the formula:

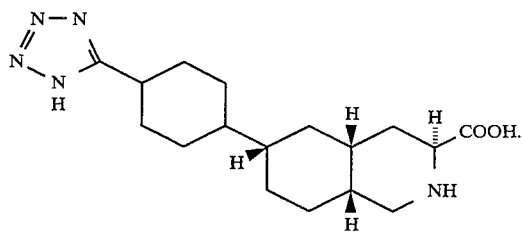

40. The compound of claim 1 of the formula:

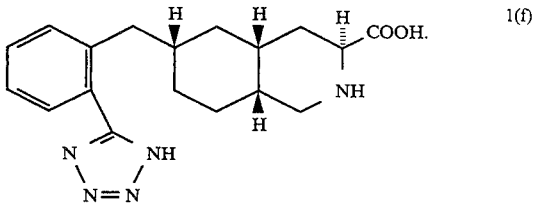

UNITED STATES PATENT AND TRADEMARK OFFICE
CERTIFICATE OF CORRECTION

PATENT NO. : 5,446,051
DATED : August 29, 1995
INVENTOR(S) : Paul L. Ornstein

It is certified that error appears in the above-indentified patent and that said Letters Patent is hereby corrected as shown below:

Column 24, line 18 should be changed
from "$R^4$ is $C_2H, S_3H, PO_3H_2$, or one of the following cyc-" to
"$R^4$ is $CO_2H$, $SO_3H$, $PO_3H_2$, or one of the following cyc"

Signed and Sealed this

Twenty-seventh Day of February, 1996

Attest:

BRUCE LEHMAN

Attesting Officer    Commissioner of Patents and Trademarks